United States Patent [19]

Singhal

[11] Patent Number: 5,068,375

[45] Date of Patent: Nov. 26, 1991

[54] SUBSTITUTED NOBLE METAL XANTHATES

[75] Inventor: Gophal H. Singhal, Baton Rouge, La.

[73] Assignee: Exxon Research & Engineering Company, Florham Park, N.J.

[21] Appl. No.: 590,889

[22] Filed: Oct. 1, 1990

[51] Int. Cl.$^5$ .............................................. C07F 15/00
[52] U.S. Cl. .................................................. 556/136
[58] Field of Search ................... 556/136, 44, 49, 114

[56] References Cited

U.S. PATENT DOCUMENTS 4,199,520 4/1980 Cosby et al. ........................ 556/136
4,241,154 12/1980 Hara et al. ....................... 556/136 X
4,279,829 7/1981 Velenyi et al. ..................... 536/136
4,927,966 5/1990 Kalman ........................... 556/136 X

*Primary Examiner*—Arthur C. Prescott
*Attorney, Agent, or Firm*—Henry E. Naylor

[57] ABSTRACT

This invention relates to the preparation of substituted noble metal xanthates having the formula $(R_1OR_2OSC_2)_nM$, where $R_1$ is an alkyl group, an alkoxy or polyalkoxy substituted alkyl group, an aryl group, or a substituted aryl group; $R_2$ is an alkylene group; M is a noble metal selected from Pt, Rh, and Ir; n is 2 when M is Pt; and n is 3 when M is Rh or Ir.

16 Claims, No Drawings

SUBSTITUTED NOBLE METAL XANTHATES

BACKGROUND OF THE INVENTION

1. Field of the Invention

The present invention relates to substituted noble metal xanthates and the method of their preparation. These xanthates can be used as precursors for catalysts for removing impurities such as nitrogen and sulfur from hydrocarbonaceous feeds.

2. Description of Related Art

Various metal xanthates are known in the art. For example, U.S. Pat. Nos. 2,037,717 and 2,037,718 concern the preparation of metal xanthates. In addition, U.S. Pat. No. 2,335,017 discloses that metal xanthates having the formula $ROCS_2M$ may be used in a lubricating oil. It is taught in that reference that M is a metal and R is an aliphatic or aromatic radical that may contain further substituted atoms or groups such as -O(alkyl).

Similarly, certain substituted metal xanthates are also known in the art. For example, the reaction of nickel methoxyethylxanthate with other compounds has been studied (see *Inorg. Chem.*, Vol. 18, no. 12, pp. 3612-15 (1979)) as has the decomposition of potassium methoxyethylxanthate (see *J. Org. Chem.* Vol. 44, no. 10, pp. 1664-9 (1989)). Also, sodium ethoxyethylxanthate and potassium ethoxy-ethylxanthate are known (see European Patent Application 131,374 and U.S. Pat. No. 3,965,137, respectively).

However, none of these publications related to the substituted noble metal xanthates of this invention.

SUMMARY OF THE INVENTION

In accordance with the present invention, there is provided substituted noble metal xanthates having the formula:

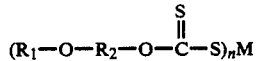

where
$R_1$ is an alkyl group (straight, branched or cyclic), an alkoxy substituted alkyl group, an aryl group, or a substituted aryl group;
$R_2$ is a straight or branched alkylene group;
M = a noble metal selected from Pt, Rh and Ir;
n = 2 when M is Pt, and
n = 3 when M is Rh or Ir.

In a preferred embodiment, both $R_1$ and $R_2$ are ethyl and M is Pt.

DETAILED DESCRIPTION OF THE INVENTION

As discussed above, the substituted noble metal xanthates of this invention have the general formula:

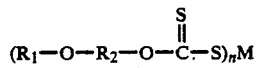

where
$R_1$ is an alkyl group (straight, branched or cyclic), an alkoxy substituted alkyl group, an aryl group, or a substituted aryl group;
$R_2$ is a straight or branched alkylene group;
M = a noble metal selected from Pt, Rh and Ir;
n = 2 when M is Pt, and
n = 3 when M is Rh or Ir.

Preferably, $R_1$ is a straight chain alkyl group, a branched chain alkyl group, or an alkoxy substituted alkyl group. Most preferably, $R_1$ comprises a straight chain alkyl group. Although the number of carbon atoms in $R_1$ could vary broadly, typically $R_1$ will have from 1 to 24, preferably from 2 to 12, and more preferably from 2 to 8, carbon atoms. Typically, $R_2$ will have from 2 to 8, preferably from 2 to 4, carbon atoms. Most preferably, $R_1$ and $R_2$ will each have from 2 to 4 carbon atoms. $R_1$ and $R_2$ together should contain a sufficient number of carbon atoms such that the substituted noble metal xanthates are soluble in hydrocarbon liquids. Typically, this will require $R_1$ and $R_2$ together to have at least 4 carbon atoms. Examples of suitable substituted groups in $R_1$ include aryl, alkylthioaryl, alkoxyaryl, and the like.

Some examples of $R_1$ are methyl, ethyl, propyl, isopropyl, butyl, isobutyl, amyl, hexyl, cyclohexyl, 2-ethylhexyl, ethoxyethyl, butoxyethyl, phenyl, butylphenyl, dodecylphenyl, methoxyphenyl, and the like. Ethyl, butyl, isobutyl, amyl, cyclohexyl, 2-ethylhexyl, ethoxyethyl, butoxyethyl, phenyl, dodecylphenyl, and methoxyphenyl are preferred. Ethyl, butyl, cyclohexyl, 2-ethylhexyl, ethoxyethyl, butoxyethyl, and dodecylphenyl are more preferred, with ethyl being the most preferred.

Non-limiting examples of $R_2$ include ethylene, propylene, isopropylene, butylene, methylpropylene, and the like. Ethylene, propylene, isopropylene, and butylene are preferred. Ethylene and isopylene are more preferred, with ethylene being most preferred.

Non-limiting examples of preferred substituted noble metal xanthates of this invention, particularly when the noble metal is platinum, include: platinum bis-1-methoxy-2-propylxanthate, platinum bis-3-methoxy-1-butylxanthate, platinum ethoxyethylxanthate, platinum butoxyethylxanthate, platinum phenoxyethylxanthate, platinum dodecyl-phenoxyethylxanthate, platinum butylphenoxyethylxanthate, platinum bis(2-ethylhexyloxyethylxanthate), and platinum cyclohexyloxyethylxanthate. Preferred substituted platinum xanthates are bis-1-methoxy-2-propylxanthate, platinum bis-3-methoxy-1-butylxanthate, platinum ethoxyethylxanthate, platinum butoxyethylxanthate, platinum ethoxyethoxyethylxanthate, platinum butoxyethoxyethylxanthate, and platinum bis(2-ethylhexyloxyethylxanthate). More preferred is platinum ethoxyethylxanthate.

The noble metals are selected from platinum, rholbdium, and iridium. Preferred are rhodium and platinum, with platinum being the most preferred.

The noble metal 2-ethoxyethylxanthato complexes of this invention are prepared by the reaction of potassium 2-ethoxyethylxanthate (KEEX) with noble metal compounds as given in Examples 1–6 in water of mixed solvents such as ethanol-water, acetone-water and the like. Usually one molar equivalent solution of a noble metal compound such, as potassium tetrachloroplatinate, in water is added to 2 to 4.5 molar equivalent of potassium 2-ethoxyethylxanthate solution in water. As given in Example 3 hereof for successful preparation of tris(2-ethoxyethylxanthato) rhodium (RhEEX), a solution of sodium hexachlororhodate in water containing 10% ethanol has to be used, and the molar equivalent of KEEX is now increased to 3-4.5. In the absence of ethanol, or similar other co-solvent, RhEEX could not be produced. On the other hand, IrEEX complexes could not be prepared by any of the methods successful for the synthesis of PtEEX and RhEEX.

The substituted noble metal xanthates of this invention are particularly suited for use in catalyst systems for hydrotreating hydrocarbonaceous materials for the removal of impurities such as sulfur and nitrogen.

This invention may be further understood by reference to the following examples which are for illustrative purposes and are not intended to restrict the scope of the instant claims.

EXAMPLE 1

Synthesis of Potassium Ethoxyethylxanthate

About 125.5 g. (2 moles) of potassium hydroxide pellets were added to an Erlenmeyer Flask containing 385 g. (4.28 moles) of ethoxyethanol and the mixture was shaken manually. The mixture became hot and turned reddish yellow as the potassium hydroxide dissolved. The mixture was then cooled in a water bath, but a significant amount of the potassium hydroxide remained undissolved. The solution was decanted into another flask and ethoxyethanol (in 100 g portions) was added to the residue with shaking and cooling.

This process was repeated until all of the potassium hydroxide had dissolved. About 180 ml. (3 moles) of carbon disulfide ($CS_2$) was added to the solution (with mechanical stirring and cooling) to form a thick viscous solution. A toluene-heptane solution (1:1) was added to the mixture and a crystalline solid precipitate was formed. The solid was collected by filtration, washed with heptane, and air dried. Solvents were removed from the filtrate and washings under reduced pressure resulted in a second solid contaminated with oil. This solid was washed well with a toluene-heptane solution to remove the oil, air dried, and then combined with the first solid to give 294.7 g. (72% conversion) of a light yellow solid product. This yellow solid product was found to be potassium 2-ethoxyethylxanthate.

EXAMPLE 2

To a magnetically stirred solution of 6.7 g of potassium 2-ethoxyethylxanthate in 200 ml. of deionized water was added a filtered solution of 4.2 g of potassium tetrachloroplatinate in 100 ml. of deionized water. The mixture turned turbid and slowly a yellow precipitate separated out. The mixture was stirred for 2.5 hrs and the resulting solid collected by filtration, washed well with deionized water and air dried. The solid was recrystallized from acetone-water to give 4.5 g of orange-yellow crystalline solid, having a melting point of 83°–84° C. A sample of the product was analyzed for chemical composition.

Analysis calculated for $C_{10}H_{18}O_4S_4Pt$: C, 22.53; H, 3.38; S, 24.65; Pt, 38.04. Found: C, 22.86; H, 3.43; S, 24.38; Pt, 37.14.

A $H_1$ NMR of sample in $CDCl_3$ (270 MHz) with TMS as internal standard was consistent with the structure; 1.25 (t, 6 H), 3.55 (q, 4 H), 3.85 (t, 4H), 4.7 (t, 4 H).

COMPARATIVE EXAMPLE 1

When the process given in Example 2 was applied for the preparation of tris(2-ethoxyethylxanthato) rhodium, the method failed and the desired product could not be obtained.

To a magnetically stirred solution of 4.2 g (0.0206 mole) of potassium 2-ethoxyethylxanthate in 100 ml of deionized water was added a solution of 1.92 g (0.005 mole) of sodium hexachlororhodate in 50 ml of deionized water. The mixture was stirred for 2 hrs. The color of the solution was reddish brown, however, no separation of solids took place. The mixture was stirred for 1 hour longer, no change was observed. To the mixture 10 ml of ethanol was added and stirring was continued for 1 hr longer, still no solid product was formed. Attempts to isolate product by concentration of the mixture under reduced pressure did not succeed.

EXAMPLE 3

Successful Preparation of RhEEX

To a magnetically stirred solution of 4.2 g (0.206 mole) of potassium 2-ethoxyethylxanthate in 100 ml of deionized water and 10 ml of ethanol was added a solution of 1.92 g (0.005 mole) of sodium hexachlororhodate in 50 ml of deionized water. The mixture slowly turned yellow with a distinct reddish brown tinge. The resulting solid was collected after 2 hrs, washed with deionized water, air dried and recrystallized from acetone-heptane to give reddish yellow solid having a melting point of 75° to 76° C., and which was identified as tris(2-ethoxyethylxanthato)Rh(III).

Analysis calculated for $C_{15}H_{27}O_6S_6Rh$: C, 30.10; H, 4.52; S, 32.11; Rh, 17.22. Found: C, 28.03; H, 4.84; S, 31.04; Rh, 16.52.

A $H_1$ NMR of sample in $D_6$ acetone (270 MHz) with TMS as internal standard was consistent with the structure; 1.15 (t, 6 H), 3.55 (q, 4 H), 3.85 (t, 4 H), 4.75 (t, 4 H).

EXAMPLE 4

Example 2 above was repeated except that 75 g of potassium 2-ethoxyethylxanthate, 34.62 g of sodium hexachlororhodate, 150 ml of ethanol, and 1200 ml of deionized water were used. Also, the reaction mixture which had turned gummy was scratched and cooled in an ice bath to facilitate solidification. The yield of the product was 52.63 g having a melting point of 74°–76° C., and a mixture melting with the product obtained in Example 2 was underpressed.

EXAMPLE 5

The preparation given in Example 2 was repeated with the exception that 70 g of potassium 2-ethoxyethylxanthate, 45 g of potassium tetrachloroplatinate, and 2000 ml. of deionized water were used. Bis(2-ethoxyethylxanthato)Pt(II) was obtained in 56.7 g quantity, m.p. 82°–84° C. A mixture melting point of this product with the product obtained in Example 2 was underpressed.

EXAMPLE 6

Attempted Synthesis of tris(2-ethoxyehylxanthato)Ir(III) (IrEEX)

Attempts to prepare IrEEX by the process given in Example 2 employed for the preparation of PtEEX or by the method given in Example 3 and used for the preparation of RhEEX using 10% ethanol were unsuccessful. In all, five attempts were made by changing the solvent compositions.

What is claimed is:

1. A substituted noble metal xanthate composition having the formula:

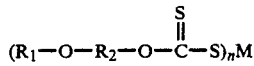

where
- $R_1$ is an alkyl group, an alkoxy substituted alkyl group, an aryl group, or a substituted aryl group;
- $R_2$ is a straight or branched alkylene group;
- M is a noble metal selected from Pt, Rh, and Ir;
- n is 2 when M is Pt; and
- n is 3 when M is Rh.

2. The xanthate composition of claim 1 wherein M is Pt.

3. The xanthate composition of claim 1 wherein $R_1$ is a straight chained alkyl group.

4. The xanthate composition of claim 1 wherein $R_1$ has from 1 to 24 carbon atoms and $R_2$ has from 2 to 8 carbon atoms.

5. The xanthate composition of claim 4 wherein $R_1$ has from 2 to 12 carbon atoms.

6. The xanthate composition of claim 5 wherein $R_1$ and $R_2$ each have from 2 t 4 carbon atoms.

7. The xanthate composition of claim 1 wherein the substituted group in $R_1$ comprises at least one member selected from the group consisting of aryl, alkylthioaryl, alkoxyaryl.

8. The xanthate composition of claim 1 wherein the substituted noble metal xanthate comprises at least one member selected from the group consisting of noble metal bis-1-methoxy-2-propylxanthate, noble metal bis-3-methoxy-1-butylxanthate, noble metal ethoxyethylxanthate, noble metal butoxyethylxanthate, noble metal ethoxyethoxyethylxanthate, noble metal butoxyethoxyethylcanthate, noble metal dodecylphenoxyethyxanthate, and noble metal bis(2-ethylhexyloxyethylxanthate).

9. The xanthate composition of claim 8 wherein the noble metal is Pt or Rh.

10. The xanthate composition of claim 9 wherein the noble metal is Pt.

11. The xanthate composition of claim 10 which is selected from platinum ethoxyethyxanthate, platinum butoxyethylxanthate, or mixtures thereof.

12. The xanthate composition of claim 11 which is platinum ethoxyethyxanthate.

13. A method of preparing a substituted platinum xanthate having the formula:

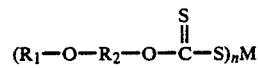

where
- $R_1$ is an alkyl group, an alkoxy substituted alkyl group, an aryl group, or a substituted aryl group;
- $R_2$ is a straight or branched alkylene group;
- M is a noble metal selected from Pt, Rh, and Ir;
- n is 2 when M is Pt; and
- n is 3 when M is Rh or Ir 14. The method of claim 13 wherein the alkoxyalkanol is ethoxyethanol, butoxyethanol, or a mixture thereof.

15. The method of claim 14 wherein the alkoxyalkanol is ethoxyethanol.

16. The method of claim 15 wherein the noble metal is platinum.

* * * * *